United States Patent [19]

Susi

[11] 3,951,912
[45] Apr. 20, 1976

[54] HYDROXYBENZYLPHOSPHONATE ANTIOXIDANTS

[75] Inventor: Peter Vincent Susi, Middlesex, N.J.

[73] Assignee: American Cyanamid Company, Stamford, Conn.

[22] Filed: Jan. 21, 1975

[21] Appl. No.: 542,760

Related U.S. Application Data

[63] Continuation-in-part of Ser. No. 458,273, April 5, 1974, abandoned.

[52] U.S. Cl. .................. 260/45.85 B; 260/45.85 S; 260/45.95 D; 260/961
[51] Int. Cl.² ........................................... C08J 3/20
[58] Field of Search ............... 260/45.85 B, 45.85 S, 260/45.95 D

[56] References Cited
UNITED STATES PATENTS 3,280,070  10/1966  DiBattista et al. ............ 260/45.95 D
3,367,870  2/1968  Spivack ........................ 260/45.95 D
3,795,700  3/1974  Song et al. ................... 260/45.85 B Primary Examiner—V. P. Hoke
Attorney, Agent, or Firm—Philip Mintz

[57] ABSTRACT

Compounds of the formula

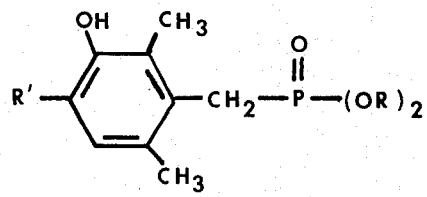

wherein R is an alkyl of 12 to 30 carbon atoms and R' is a branched-chain alkyl of 3 to 12 carbon atoms and their use alone or in combination with a secondary stabilizer, such as distearyl thiodipropionate, dilauryl thiodipropionate, or pentaerythritol tetrakis(3-n-dodecylthiopropionate), for stabilizing polyolefin or acrylonitrile-butadiene-sytrene resin.

9 Claims, No Drawings

HYDROXYBENZYLPHOSPHONATE ANTIOXIDANTS

This application is a continuation-in-part of application Ser. No. 458,273, filed Apr. 5, 1974, now abandoned.

This invention relates to novel compounds useful for stabilizing organic materials normally subject to oxidative degradation, such as polyolefins and acrylonitrilebutadienestyrene resins (hereinafter called "ABS resins"). More particularly, it relates to stabilizing such materials with effective amounts of novel benzyl phosphonates of the formula:

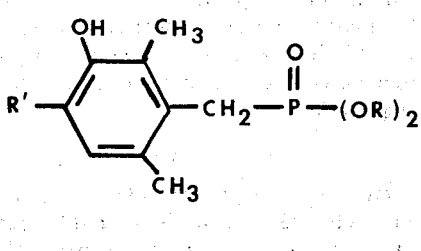

wherein R is an alkyl group of 12 to 30 carbon atoms and R' is a branched-chain alkyl of 3 to 12 carbon atoms. Especially useful are compounds wherein R is dodecyl or octadecyl and wherein R' is tertiary-butyl. Greatly superior protection of polypropylene is achieved if a secondary stabilizer, such as distearyl thiodipropionate, dilauryl thiodipropionate, or pentaerythritol tetrakis(3-n-dodecylthiopropionate), is also incorporated therein.

Prior to the present invention, it was known that compounds of the formula:

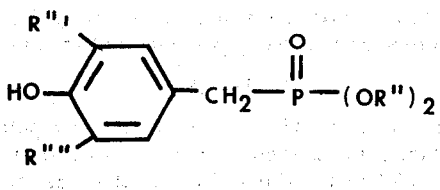

wherein R' is an alkyl group of 1 to 12 or 12 to 24 carbon atoms and R'' and R''' are both alkyls, which may be branched-chain alkyls, were useful antioxidants (See U.S. Pat. Nos. 3,006,945; 3,281,505; and 3,367,870). An especially preferred and commercially available compound of this class is Irganox 1093, wherein R'' is octadecyl and wherein R''' and R'''' are tertiary-butyl (See Example 9 of U.S. Pat. Nos. 3,281,505 and 3,367,870). These compounds, while useful, are not perfect. It was an object of the present invention to provide novel compounds which would be superior antioxidants.

It will be noted that several differences between the novel compounds of the present invention and the prior art compounds exist; viz., (a) the hydroxy group in these novel compounds is meta to the methylene-phosphonate group on the benzene ring (instead of para as in the prior art), (b) the two positions ortho to the methylene-phosphonate group are methyl-substituted in these novel compounds (instead of being unsubstituted as in the prior art), etc. These differences in structure lead to the superior properties of the compounds of the present invention, which superior properties will be discussed and demonstrated in the following examples.

The compounds of this invention can be prepared by reacting a trialkyl phosphite of the formula $P(OR)_3$, wherein R is as above defined with a phenolic benzyl halide of the formula:

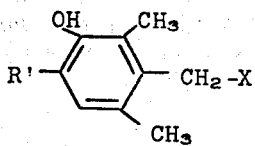

wherein R' is as above defined and X is a halogen, such as chlorine or bromine. Trialkyl phosphites are known compounds, disclosed in U.S. Pat. Nos. 3,006,945; 3,281,505; and 3,367,870. The meta-hydroxy phenolic benzyl halides are also known compounds, disclosed in U.S. Pat. Nos. 3,660,352 and 3,704,326.

The compounds of this invention can also be prepared by reacting an alkali metal salt of a dialkyl hydrogen phosphite of the formula

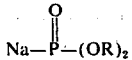

wherein R is as defined above with the phenolic benzyl halide wherein the hydroxy group is protected by a blocking group, e.g. acetoxy, after which the hydroxy group is regenerated by caustic hydrolysis (as in Example 2, infra). Dialkyl hydrogen phosphites are known compounds, disclosed in U.S. Pat. Nos. 3,281,505 and 3,367,870.

These novel compounds are incorporated into the organic materials to be protected by any conventional method, such as by milling, Banbury mixing, extrusion, swelling, stirring, kneading, etc. They are usually used in a concentration of from about 0.01 to 2.0 percent on weight of substrate, preferably from about 0.1 to about 0.5 percent. When these compounds are used with a secondary stabilizer, such as distearyl thiodipropionate, dilauryl thiodipropionate, or pentaerythritol tetrakis(3-n-dodecylthiopropionate), about 0.01 to about 2.0 percent of the secondary stabilizer can be used. Other conventionally used compounding additives, such as plasticizers, fillers, ultraviolet absorbers, dyes, pigments, flame retardants, etc. may also be added.

The secondary stabilizers distearyl thiodipropionate, and dilauryl thiodipropionate are commercially available compounds. The secondary stabilizer pentaerythritol tetrakis(3-n-dodecylthiopropionate) and a method for its preparation can be found in Example 4 of U.S. Pat. No. 3,758,549, which patent describes its use (in Example 5) alone or in combination with certain compounds to stabilize polypropylene against thermal degradation.

EXAMPLE 1

A mixture of 0.1 mole (58.7 grams) of tridodecyl phosphite and 0.1 mole (22.65 grams) of 4-t-butyl-3-hydroxy-2,6-dimethylbenzyl chloride was heated at 180°–240°C. over a period of 3 hours. The dodecyl chloride formed during the reaction was removed by vacuum distillation and the product, didodecyl 4-t-butyl-3-hydroxy-2,6-dimethylbenzylphosphonate, was isolated by chromatography on alumina using a mixture of hexane/chloroform (1:2) and chloroform, respectively.

Similarly, di(2-ethylhexyl) 4-t-butyl-3-hydroxy-2,6-dimethylbenzylphosphonate was prepared using 0.1 mole of tris-(2-ethylhexyl) phosphite in place of tridodecy phosphite.

Similarly, diethyl 4-t-butyl-3-hydroxy-2,6-dimethylbenzylphosphonate was prepared using 0.1 mole of triethyl phosphite in place of tridodecy phosphite.

EXAMPLE 2

Dioctadecyl phosphite (29.35 grams, 0.05 mole) in 50 milliliters of benzene was added to 1.2 grams (0.05 mole) of sodium hydride in 150 milliliters of hexane. To this mixture was added 13.4 grams (0.05 mole) of 4-t-butyl-3-acetoxy-2,6-dimethylbenzyl chloride in 50 milliliters of benzene. The hexane/benzene was removed by distillation and replaced by 150 milliliters of dimethylformamide. The reaction mixture was heated for 18 hours at 118°C., cooled, then added to 600 milliliters of cold water, forming a precipitate. The soft precipitate was recovered and dried, yielding 26 grams of a yellow congealed residue, melting point 30°–32°C. Purification by chromatography on silica gel gave 25 grams of dioctadecyl 4-t-butyl-3-acetoxy-2,6-dimethylbenzylphosphonate. This was hydrolyzed with caustic in a 5:1 alcohol/water mixture by refluxing for 30 minutes. The product, dioctadecyl 4-t-butyl-3-hydroxy-2,6-dimethylbenzylphosphonate, was isolated by chromatography on alumina using chloroform. Recrystallization from acetone gave pale yellow crystals, melting point 70°–72°C. Analysis: Calculated: C=75.77, H=11.98, P=4.0. Found: C=75.06, H=12.35, P=3.91.

Similarly, following the above procedure, didocosyl 4-t-butyl-3-hydroxy-2,6-dimethylbenzylphosphonate is prepared using didocosyl phosphite in place of the dioctadecyl phosphite.

EXAMPLE 3

The compounds of the preceding examples were incorporated into unstabilized polypropylene in amounts of 0.2% on weight of polymer by milling at 170°–180°C. on a two-roll mill. The milled samples were then compression molded into films 15 mils in thickness. These were aged in a forced-draft oven at 140°C. and the efficiency of the compound as an antioxidant was determined by noting the time in hours to embrittlement at this temperature. The results are shown in the following table.

Table 1

| Compound* | Hours to brittle point |
|---|---|
| 2 | 2–16 |
| 8 | 50–120 |
| 12 | 529–545 |
| 18 | 1726–1746 |

*The numeral used to identify the compound is the number of carbon atoms in the R group in the formula

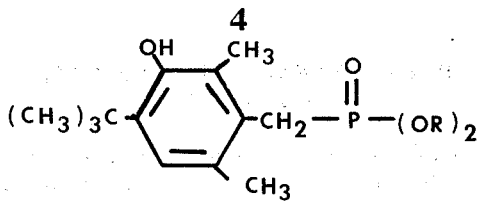

where R is an alkyl group.

The data in Table 1 show that the dioctadecyl and the didodecyl esters are greatly superior to the diethyl and dioctyl esters and that the dioctadecyl ester is greatly superior to the didodecyl ester. This is quite surprising since the alkyl groups would be expected to be inert parts of these molecules and use of larger alkyl groups with the same concentration of additive in the polymer would result in lower concentrations of the active portions of the molecules in the polymer, leading one to expect reduced effectiveness on an equal weight basis for the molecules containing larger R groups, contrary to the foregoing findings.

EXAMPLE 4

In the same manner as in Example 3, a comparison was made of a commercially available additive, Irganox 1093, (dioctadecyl 3,5-di-t-butyl-4-hydroxybenzylphosphonate) and the dioctadecyl ester of Example 2, by incorporating 0.2% on weight of polymer of each in separate samples of unstabilized polypropylene and noting the hours to embrittlement of 15 mil films on aging at 140°C. in a forced air oven. The results are shown in the following table.

Table 2

| Compound | Hours to brittle point |
|---|---|
| Irganox 1093 | 1066–1079 |
| Example 2 | 1726–1746 |

The data in Table 2 show that the meta-hydroxy compound of the present invention very much superior to the closest para-hydroxy compound of the prior art.

EXAMPLE 5

A series of samples were prepared by incorporating, in the manner of Example 3, various concentrations of Irganox 1093 or the dioctadecyl ester of Example 2, alone or in combination with a secondary stabilizer, distearyl thiodipropionate (STDP), in unstabilized polypropylene and noting the hours to embrittlement of 15 mil films of such samples on aging at 150°C in a forced-air oven. The results are shown in the following table.

Table 3

| Compound (concentration) | Hrs. to brittle pt. |
|---|---|
| Irganox 1093 (0.1%) | 80–96 |
| Irganox 1093 (0.2%) | 96–104 |
| Example 2 (0.1%) | 144–160 |
| Example 2 (0.2%) | 248–256 |
| Example 2 (0.5%) | 570–591 |
| Irganox 1093 (0.05%) + STDP (0.15%) | 770–786 |
| Example 2 (0.05%) + STDP (0.15%) | 1825–1841 |
| Irganox 1093 (0.1%) + STDP (0.25%) | 1007–1023 |
| Example 2 (0.1%) + STDP (0.25%) | 1936–1953 |

The data in Table 3 show that the meta-hydroxy compound of the present invention is very much superior to the closest para-hydroxy compound of the prior art at various concentrations whether used alone or in combination with a secondary stabilizer, such as distearyl thiodipropionate, and that the use of such a secondary stabilizer greatly improves the efficacy of both compounds spectacularly.

EXAMPLE 6

A pair of samples of 15 mil films of polypropylene, prepared as in Example 5, containing distearyl thiodipropionate in combination with either Irganox 1093 or the octadecyl ester of Example 2, was refluxed in 200 milliliters of water for 7 hours and the water was removed for a first cycle. Then, the water was replaced and the samples were refluxed for another 7 hours, and the water was removed, for a second cycle. This was repeated until either 6 or 15 such cycles were completed, after which the samples were aged in a forced-air oven at 150°C. until embrittlement. The results are shown in the following table.

Table 4

| Compound (concentration) | Hours to brittle point After extraction in boiling water | |
|---|---|---|
| | 6 cycles | 15 cycles |
| Irganox 1093 (0.1%) + STDP (0.25%) | 1128–1183 | 759–767 |
| Example 2 (0.1%) + STDP (0.25%) | 1846–1854 | 1197–1247 |

The data in Table 4 show that, even after multiple extractions with boiling water, the meta-hydroxy compound of the present invention affords protection to polypropylene which is much superior to the protection afforded by the para-hydroxy compound of the prior art.

EXAMPLE 7

Titanium dioxide (5.0% on weight of polymer) and zinc stearate (1.0% on weight of polymer) were incorporated into unstabilized ABS resin, alone or with the octadecyl ester of Example 2 (0.5% on weight of polymer) by milling at 170°–180°C. and formed into 50 mil plaques by compression molding at 180°–190°C. After aging in a forced-draft oven at 150°C. for various times, the increase in the Yellowness Index ($\Delta$ YI) was measured using a Hunter Color Difference Meter. The results are shown in the following table.

Table 5

| Sample | $\Delta$YI after aging for | | |
|---|---|---|---|
| | 16 hrs. | 24 hrs. | 46 hrs. |
| Control | 40 | — | — |
| With octadecyl ester | 11 | 13 | 18 |

The data in Table 5 show that the octadecyl ester of Example 2 inhibits discoloration of ABS resin on exposure to air at elevated temperature.

I claim:

1. A composition comprising a polyolefin containing a stabilizing quantity of (a) a compound of the formula:

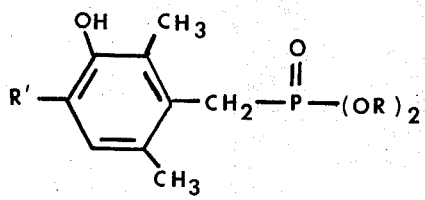

wherein R is an alkyl group of 12 to 30 carbon atoms and $R_1$ is a branched-chain alkyl of 3 to 12 carbon atoms and (b) a secondary stabilizer selected from the group consisting of distearyl thiodipropionate, dilauryl thiodipropionate, and pentaerythritol tetrakis(3-n-dodecylthiopropionate).

2. A composition as defined in claim 1 wherein said stabilizing quantity is 0.01 to 2.0 percent on weight of polyolefin of said compound and 0.1 to 1.0 percent on weight of polyolefin of said secondary stabilizer.

3. A composition as defined in claim 1 wherein said secondary stabilizer is distearyl thiodipropionate or dilauryl thiodipropionate.

4. A composition as defined in claim 1 wherein said polyolefin is polypropylene.

5. A composition as defined in claim 1 wherein R is dodecyl.

6. A composition as defined in claim 1 wherein R is octadecyl.

7. A composition as defined in claim 1 wherein R' is t-butyl.

8. A composition as defined in claim 7 wherein R is dodecyl.

9. A composition as defined in claim 7 wherein R is octadecyl.

* * * * *